United States Patent
Ramsauer

(10) Patent No.: US 9,131,914 B2
(45) Date of Patent: Sep. 15, 2015

(54) COMPRESSION PLATE FOR TOMOSYNTHESIS

(75) Inventor: Martin Ramsauer, Pyrbaum (DE)

(73) Assignee: Siemens Aktiengesellschaft, München (DE)

( * ) Notice: Subject to any disclaimer, the term of this patent is extended or adjusted under 35 U.S.C. 154(b) by 295 days.

(21) Appl. No.: 13/696,041

(22) PCT Filed: May 3, 2011

(86) PCT No.: PCT/EP2011/056992
§ 371 (c)(1),
(2), (4) Date: Nov. 2, 2012

(87) PCT Pub. No.: WO2011/138294
PCT Pub. Date: Nov. 10, 2011

(65) Prior Publication Data
US 2013/0051520 A1      Feb. 28, 2013

(30) Foreign Application Priority Data

May 3, 2010   (DE) .......................... 10 2010 019 023

(51) Int. Cl.
*A61B 6/04*   (2006.01)
*A61B 6/00*   (2006.01)
*A61B 6/02*   (2006.01)

(52) U.S. Cl.
CPC ............... *A61B 6/502* (2013.01); *A61B 6/0414* (2013.01); *A61B 6/02* (2013.01)

(58) Field of Classification Search
CPC ......... A61B 6/502; A61B 6/0414; A61B 6/02
USPC .................................................. 378/37, 208
See application file for complete search history.

(56) References Cited

U.S. PATENT DOCUMENTS

| | | | |
|---|---|---|---|
| 6,985,554 B2 | 1/2006 | Wikander | |
| 7,891,874 B2 | 2/2011 | Standar | |
| 7,978,812 B2 | 7/2011 | Thaler | |
| 2004/0125912 A1* | 7/2004 | Wikander | ........................ 378/37 |

(Continued)

FOREIGN PATENT DOCUMENTS

| | | |
|---|---|---|
| CN | 101438964 A | 5/2009 |
| DE | 10 346 966 A1 | 5/2004 |

(Continued)

OTHER PUBLICATIONS

German Office Action dated Aug. 26, 2011 for corresponding German Patent Application No. DE 10 2010 019 023.3 with English translation.

(Continued)

*Primary Examiner* — Michael Maskell
(74) *Attorney, Agent, or Firm* — Lempis Summerfield Katz LLC

(57) ABSTRACT

A compression plate for tomosynthesis images using an X-ray apparatus designed to take the tomosynthesis images is provided. The compression plate includes an upper area. The width of the upper area is dimensioned such that, for all X-ray images taken during tomosynthesis of a female breast compressed by the compression plate, X-rays substantially penetrate the compression plate. The compression plate also includes a lower area. An average width of the lower area is smaller than an average width of the upper area. The lower area includes a surface of smaller width than the width of the upper area for the compression of the female breast.

7 Claims, 5 Drawing Sheets

(56) References Cited

U.S. PATENT DOCUMENTS

| | | |
|---|---|---|
| 2004/0202360 A1* | 10/2004 | Besson .................. 382/131 |
| 2006/0262899 A1 | 11/2006 | Al-Khalidy et al. |
| 2007/0223652 A1 | 9/2007 | Galkin |
| 2008/0080668 A1 | 4/2008 | Kashiwagi |
| 2008/0152077 A1 | 6/2008 | Ramsauer |
| 2009/0299218 A1* | 12/2009 | Holler et al. .................. 600/567 |
| 2010/0316186 A1* | 12/2010 | Hyvarinen ................ 378/37 |

FOREIGN PATENT DOCUMENTS

| | | |
|---|---|---|
| DE | 10 2006 059 740 A1 | 6/2008 |
| DE | 10 2007 056 433 A1 | 6/2009 |
| DE | 10 2008 011 154 A1 | 9/2009 |
| WO | WO 2009/068732 A1 | 6/2009 |

OTHER PUBLICATIONS

PCT International Search Report dated Jul. 6, 2011 for corresponding PCT/EP2011/056992 with English translation.

Chinese Office Action dated May 20, 2014 for corresponding Chinese Patent Application No. 201180022235.5 with English translation.

* cited by examiner

COMPRESSION PLATE FOR TOMOSYNTHESIS

The present patent document is a §371 nationalization of PCT Application Ser. No. PCT/EP2011/056992, filed May 3, 2011, designating the United States, which is hereby incorporated by reference. This patent document also claims the benefit of DE 10 2010 019 023.3, filed on May 3, 2010, which is also hereby incorporated by reference.

BACKGROUND

The present embodiments relate to a compression plate for tomosynthesis images using an x-ray device configured to take tomosynthesis images.

X-ray devices are widely used in medical diagnosis. In some cases, devices for x-ray diagnosis are specifically embodied for particular examinations in order to take account of the particular requirements during the examination. One example of a specific diagnostic device is the mammography device for the examination of breast tissue in patients. To enhance the quality of the images acquired, the breast to be examined is compressed with the aid of a compression plate. During a mammography examination, x-rays are emitted by an x-ray source, penetrate the compressed breast and are subsequently detected by a detector.

Conventional examinations using mammography may include a single image or two images acquired from different angles (e.g., mediolateral oblique (MLO) and cranio-caudal (CC) acquisition). With this type of imaging, the attenuation of the x-rays on penetration of the tissue is detected. The attenuation is dependent on the density of the penetrated tissue. On account of the changed density of diseased tissue, diseased tissue may be diagnosed from the acquired images. An important limitation of this process lies in the fact that information about a three-dimensional object (e.g., breast tissue) is obtained by a detector with a resolution in two dimensions. In the direction of the x-ray beam (e.g., perpendicular to the detector surface) only general information (e.g., overall attenuation) is obtained (e.g., practically no resolution exists). This limitation may lead to misdiagnoses.

Tomosynthesis is a development of conventional mammography that allows a resolution orthogonal to the detector surface. During the course of tomosynthesis, the x-ray source follows a trajectory (e.g., an arc of e.g. 50°). On passage through the trajectory, images are acquired from different angles (e.g., 10-50 images). A three-dimensional image of the object under examination may be obtained or reconstructed from this plurality of images by reconstruction algorithms. The three-dimensional image makes better diagnosis and localization of diseased tissue possible.

Components of the mammography device are to be adapted for tomoacquisition. For example, specific requirements are produced for the compression plates used in the imaging. For example, US 2006/0262899 A1 discusses adaptations of a compression paddle with respect to tomoacquisition (e.g., embodiment of the paddle for preventing shadows at the edges).

The general situation for acquiring tomosynthesis images is shown in FIG. 2. Disposed on a holder 3 are an object table 1 (e.g., containing the detector) and a compression plate 2, using which the breast 11 to be examined is compressed. The x-ray source follows a trajectory 10, while the tomosynthesis images are being acquired. Positions 101, 102, 103 . . . are marked on the trajectory, for which an x-ray image is made in each case. These positions, for example, reflect the location of the focus of the x-ray source for these images. The spreading out of the x-ray beam is shown in the figure for three positions 101, 110 and 120. The shape of the x-ray beam is in most cases a fan or a cone. On account of the images being acquired from different angular positions, the compression plate 2 is to be wider than if only one central image (e.g., position 110) were made.

SUMMARY AND DESCRIPTION

The present embodiments may obviate one or more of the drawbacks or limitations in the related art. For example, an operating sequence may be improved during tomosynthesis examinations.

During tomosynthesis, usual wide compression plates hinder the process of positioning the breast because the access or the room for positioning is restricted by the wide plate.

In one embodiment, a compression plate that is embodied in two areas or sections is provided.

One area or section is an upper area when the plate is attached to the device (e.g., a tomosynthesis device). The width of the upper area is dimensioned such that, for all x-ray images acquired during a tomosynthesis of a female breast compressed by the plate, the x-rays substantially penetrate the plate (e.g., through the dimensions of the upper area, the x-rays mapping the object (e.g., a female breast) during a tomoacquisition for the various imaging positions substantially fully penetrate the plate). This property of covering the entire irradiation field of the x-rays is common to the compression plate of the present embodiments and compression plates conventionally used for tomosynthesis. The term "substantially" may take the fact that absorption also takes place in the plate and possible imprecisions in the beam focusing or a spreading out of the beam, in which the non-significant radiation components for the acquisition go past the plate, into account.

The first area may, for example, viewed from the side (e.g., from the front, right, left and behind in relation to the angle of view of a patient during the imaging), correspond to or be similar to conventional compression plates used for tomosynthesis with regard to shape.

In addition, a lower area (e.g., a lower section) is provided when the plate is attached to the device. An average width of the lower area is smaller than an average width of the upper area. The lower area also has a surface with a smaller width than the width of the upper area for the compression of the female breast. The surface is in contact with the breast during compression.

More space is created laterally by the lower area with a smaller width, so that access to a breast to be examined is made easier. The operating personnel may place the breast to be examined more easily or adjust the position of the breast, which contributes to improving the workflow.

The average width of the lower area may be significantly smaller than the maximum width (e.g., in the range of half or less than half of the maximum width). The surface that is in contact with a breast being examined may have the smallest width. In one embodiment, the lower area tapers towards the bottom.

The overall shape of the plate may be defined so that the upper area and the lower area are raised above one another (e.g., when viewed from the side, the upper area and the lower area form the approximate shape of a step). The upper area and the lower area may, however, also have a shape, in which the upper area and the lower area merge into one another continuously (e.g., only in relation to specific perspectives).

In one embodiment, the boundary between the two areas may be defined differently or merge.

In one embodiment, edges arising for compression in the periphery of the surface are rounded, tapered or chamfered in order to avoid the dangers to the tissue under examination from the existence of sharp edges.

The compression plate may, for example, be manufactured by injection molding or deep-drawing methods and may be formed by polyethylene terephthalate (PET).

DETAILED DESCRIPTION OF THE DRAWINGS

Figure 1:
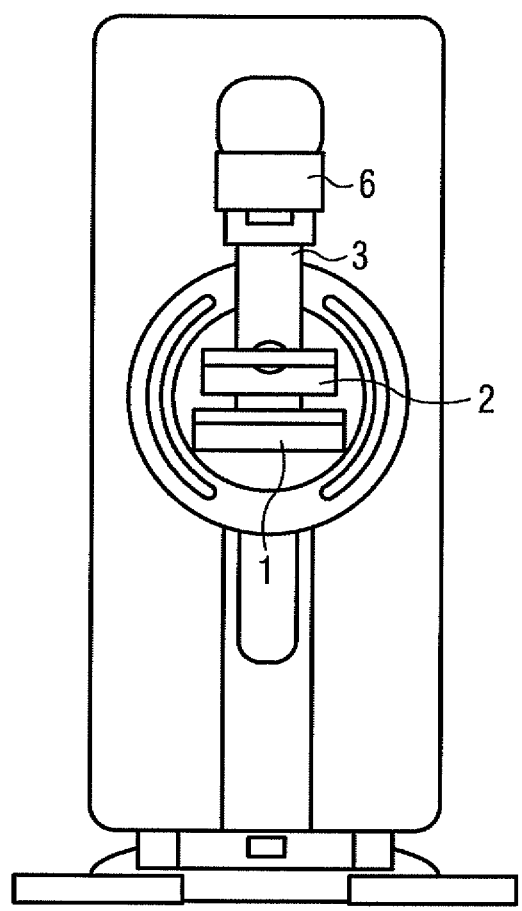
FIG. 1 shows a frontal view of one embodiment of a mammography device.

FIG. 1 shows a frontal view of one embodiment of a mammography device. Radiation is emitted from an x-ray source 6. The radiation is detected by a detector disposed in an object table or bucky cover 1. Breast tissue is compressed between the object table 1 and a compression plate 2 for the task. The compression plate 2 is attached to a holder 3 that is configured for the compression process.

Figure 2:
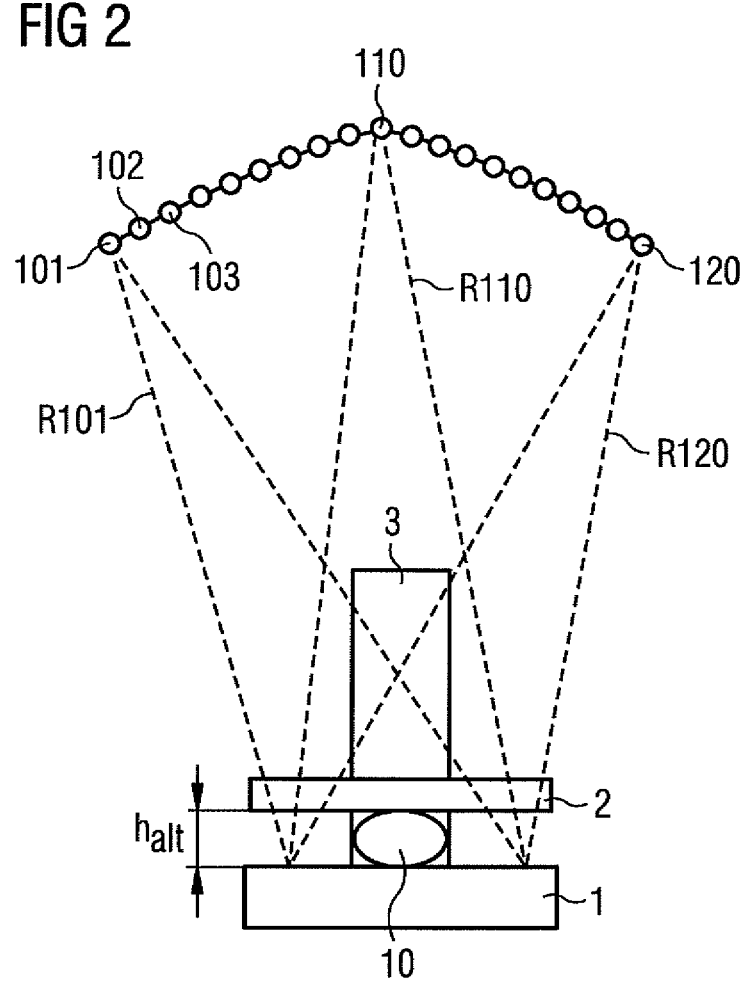
FIG. 2 shows a schematic diagram of a conventional tomoacquisition.
Figure 3:
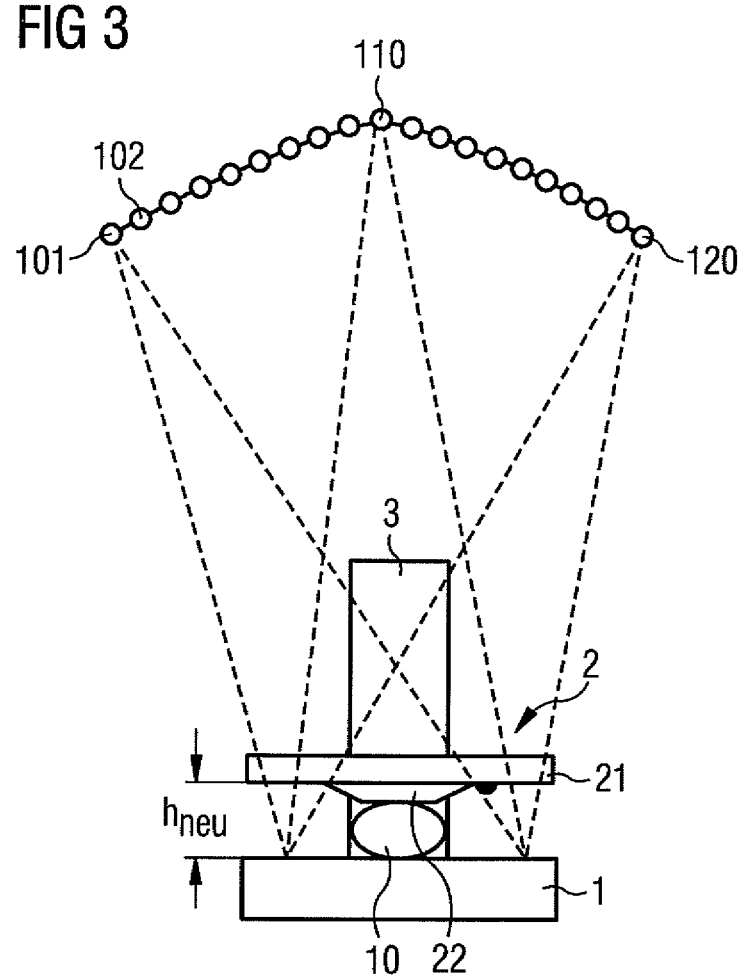
FIG. 3 shows a tomoacquisition with one embodiment of a compression plate.

FIG. 2 shows the situation in a conventional, tomoacquisition. Because of the acquisition from different angular positions (e.g., minus 25° to plus 25°), the compression plate 2 is embodied wider than for conventional acquisitions. Because of a restricted distance $h_{alt}$ between the object table 1 and the compression plate 2, operating personnel is restricted during breast positioning on account of the wide compression plate 2. One embodiment of a compression plate is provided. The advantage of the compression plate is shown in FIG. 3. The compression plate includes an area 21 or an indentation having the width of compression plates used conventionally in tomosynthesis. The compression plate has a second area 22 that has a significantly smaller width and is intended to be placed onto the breast under examination. The distance between the first area 21 in the object table 1 $h_{neu}$ is greater than the comparable distance of conventional tomoacquisitions. This makes access and thus the process of placing and compressing the breast easier for the operating personnel.

Figure 4:
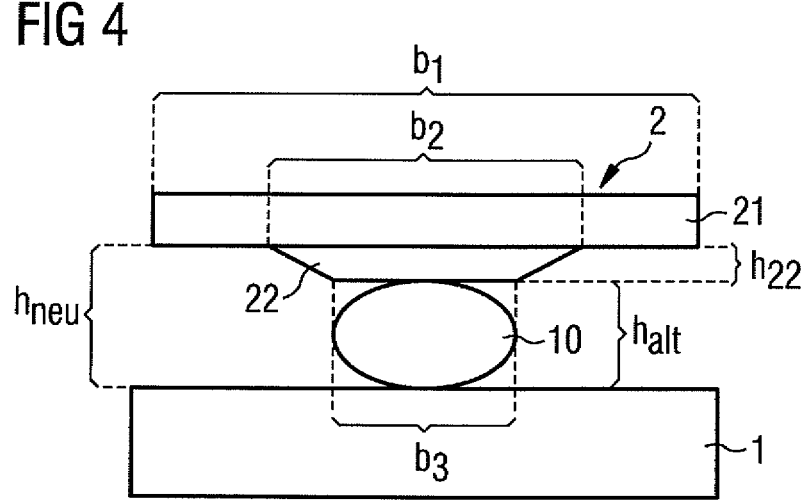
FIG. 4 shows an enlarged section from FIG. 3.

FIG. 4 shows an enlarged section from FIG. 3, on the basis of which the relationships of dimensioning individual elements will be presented. The first area 21 of the compression plate 2 has a width $b_1$. The second area 22 tapers towards the bottom. At the top, the second area 22 has the width $b_2$, and at the bottom, the second area 22 has the width $b_3$ (e.g., a lower width). The lower width $b_3$ is selected with respect to the typical extent of a female breast. The average width of the second area 22 is thus $(b_2+b_3)/2$. The height of the second area 22 is $h_{22}$. In a lateral area of the object table 1 or of the compression plate 2, the distance is $h_{neu}=h_{alt}+h_{22}$ (e.g., the height of the second area $h_{22}$ is also obtained, and thus, the access to the breast 10 under examination is improved).

Figure 5:
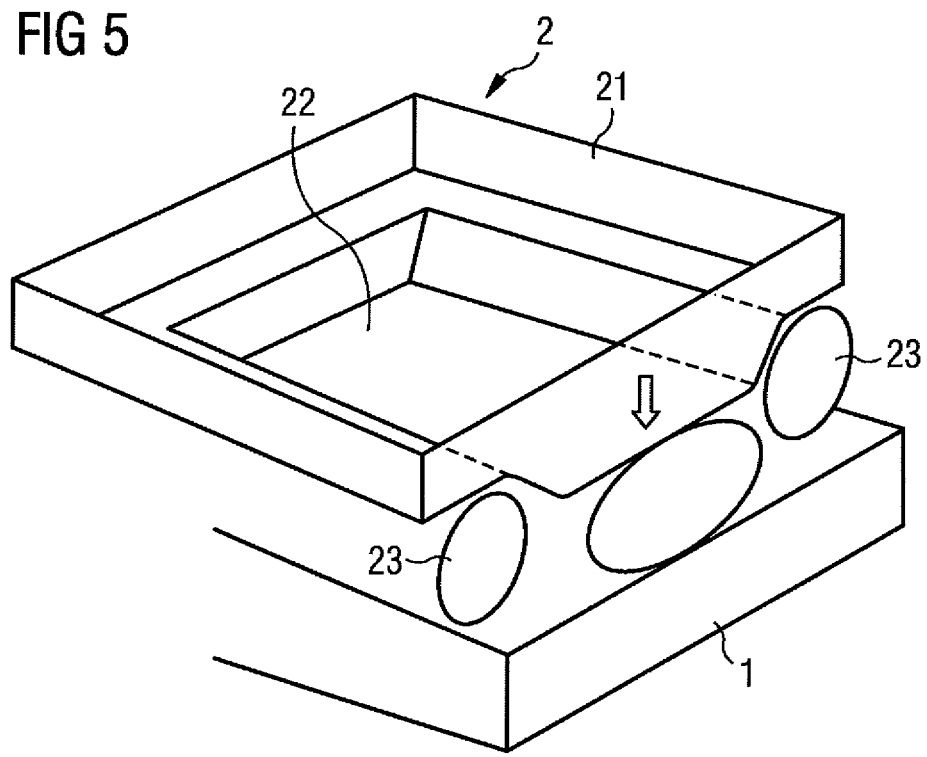
FIG. 5 shows one embodiment of a compression plate.

FIG. 5 shows one embodiment of a compression plate 2 in a perspective view. The compression plate 2 has a first area 21 that has a greater width and a second area 22 that has a smaller width and is intended for breast compression. As shown in FIG. 5, the compression plate 2 is not massive but includes a correspondingly shaped, comparatively thin layer. From the front (e.g., from the direction of view of the patient), the compression plate 2 has a profile that tapers in the second area. To a side and behind, the compression plate 2 is shaped like a truncated pyramid. The compression force acts in the direction of the arrow 22 on the breast 10 indicated. Next to the breast, because of the reduced width, there is additional space 23 for breast positioning between the compression plate 2 and the object table 1.

Figure 6:
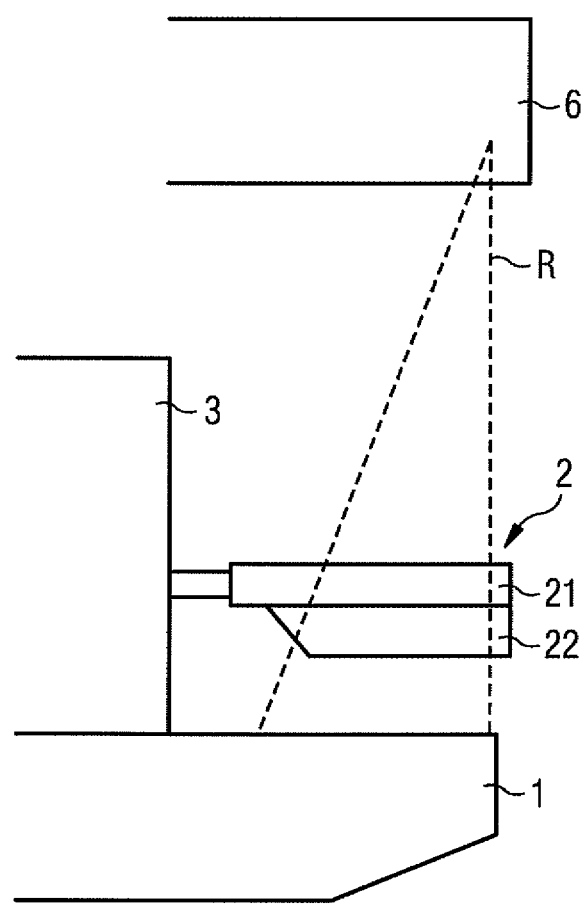
FIG. 6 shows a side view of a mammography device with one embodiment of a compression plate.

FIG. 6 shows a side view of a mammography device with one embodiment of a compression plate 2. A beam R is emitted from an x-ray tube or x-ray source 6 that is detected in the object table 1 by a detector. For compressing the breast, one embodiment of a compression plate 2 including areas 21 and 22 is attached to a holder or compression unit 3. This view shows that in the embodiment of the compression plate 2, the second area 22 not only has a smaller width but also a smaller length, with the length being defined by the direction of view of a patient to be examined.

The invention is not restricted to the exemplary embodiments. Further embodiments and developments of a compression plate for tomosynthesis may be deduced by the person skilled in the art from the general teaching of the present application.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A compression plate for tomosynthesis imaging using an x-ray device configured for the generation of tomosynthesis images, the compression plate comprising:
   an upper area when the compression plate is attached to the x-ray device, the width of the upper area being dimensioned such that, for all x-ray images acquired during a tomosynthesis of a female breast compressed by the compression plate, x-rays substantially penetrate the compression plate; and
   a lower area when the compression plate is attached to the x-ray device, an average width of the lower area being smaller than an average width of the upper area, the lower area having a surface of smaller width than the width of the upper area for the compression of the female breast,
   wherein the upper area comprises (1) an upper area top having an upper area perimeter and the width of the upper area and (2) an upper area bottom having the upper area perimeter and the width of the upper area,
   wherein the lower area comprises (1) a lower area top having a lower area top perimeter and a lower area top width and (2) a lower area bottom having a lower area bottom width,
   wherein the lower area top is adjacent to the upper area bottom,
   wherein the lower area top width is less than the width of the upper area, and
   wherein the lower area top perimeter is less than the upper area perimeter, and the lower area top perimeter does not extend beyond the upper area perimeter as viewed in a direction from an x-ray source to an x-ray detector of the x-ray device; wherein the lower area tapers towards the bottom of the lower area such that the lower area bottom width is less than the lower area top width.

2. The compression plate as claimed in claim 1, wherein edges occurring for compression are rounded in an edge area of the surface.

3. The compression plate as claimed in claim 1, wherein the compression plate is manufacturable by injection molding or deep drawing methods.

4. The compression plate as claimed in claim 1, wherein the compression plate is formed from polyethylene terephthalate.

5. The compression plate as claimed in claim 2, wherein the compression plate is manufacturable by injection molding or deep drawing methods.

6. The compression plate as claimed in claim 2, wherein the compression plate is formed from polyethylene terephthalate.

7. The compression plate as claimed in claim 3, wherein the compression plate is formed from polyethylene terephthalate.

* * * * *